United States Patent [19]

Esposito

[11] Patent Number: 4,822,407

[45] Date of Patent: Apr. 18, 1989

[54] DILUTANT FOR NON-AGRICULTURAL INDUSTRIAL HERBICIDES

[75] Inventor: James E. Esposito, Chalfont, Pa.

[73] Assignee: Asplundh Tree Expert Co., Willow Grove, Pa.

[21] Appl. No.: 49,036

[22] Filed: May 6, 1987

Related U.S. Application Data

[63] Continuation of Ser. No. 697,952, Feb. 4, 1985, abandoned.

[51] Int. Cl.$^4$ ............................................. A01N 25/02
[52] U.S. Cl. .................................. 71/94; 71/DIG. 1; 514/772; 514/937; 514/946
[58] Field of Search .............. 71/DIG. 1, 94; 514/772, 514/939, 946

[56] References Cited

U.S. PATENT DOCUMENTS

| | | | |
|---|---|---|---|
| 3,068,087 | 12/1962 | Davis | 71/DIG. 1 |
| 3,190,740 | 6/1965 | Wolter | 71/DIG. 1 |
| 3,997,322 | 12/1976 | Ratledge | 71/DIG. 1 |

FOREIGN PATENT DOCUMENTS 2057265 4/1981 United Kingdom .

OTHER PUBLICATIONS

Warren, Industrial Vegetation, vol. 12, No. 2 (1980) pp. 23–28.
Warren, Down to Earth vol. 38 No. 2 (1982) pp. 12–24.

*Primary Examiner*—Catherine L. Mills
*Attorney, Agent, or Firm*—Ferrill and Logan

[57] ABSTRACT

A dilutant for industrial herbicides applied to non-agricultural areas is disclosed in which a combination of a hydrocarbon filler, lecithin, and a mixture of other chemicals creates a dilutant with a strong affinity for emulsifiable and oil-soluble industrial herbicides, insecticides, and fungicides, and which dilutant is capable of penetrating tree bark and woody plant tissue while retaining the active ingredients and allowing the active ingredients to move upward within the xylem of the plant and downward within the phloem of the plant.

9 Claims, No Drawings

DILUTANT FOR NON-AGRICULTURAL INDUSTRIAL HERBICIDES

The present application is a continuation of U.S. patent application Ser. No. 697,952, filed Feb. 4, 1985, now abandoned.

BACKGROUND OF THE INVENTION

This invention relates to dilutants for industrial herbicides intended to be used for basal bark and cut surface treatment in non-agricultural applications. More specifically, it relates to a basal oil dilutant which has an unusual ability to penetrate bark and woody plant tissue and carry a variety of herbicides along with it, as well as allowing the herbicide to move upwards within the plant through the xylem and downward within the plant through the phloem.

Dilutants presently employed are not particularly effective, have undesirable side effects, and are limited in their range of applications. Fuel oils, the most common nonagricultural dilutants, are not remarkably efficient solvents of herbicides; accordingly, large quantities of fuel oils are required to carry an operative amount of herbicide (i.e. on the order of 50–100 parts fuel oil to every 1 part herbicide), and separation may occur during storage or handling, particularly at low temperatures. Moreover, the fuel oils do not tend to readily penetrate plant bark or woody material, thus requiring either frilling or cutting work during basal bark application, or the use of very high volumes of herbicide-carrier solution. The use of fuel oils, therefore, results in large amounts of chemical waste and escalated handling and application costs. Additionally, the use of fuel oils produces offensive odors and may produce off-target damage due to drift and volatility which all are detrimental to public relations and can result in claims against the user. Additionally, the use of large quantities of fuel oil depletes the supply necessary for home and industrial heating.

Other classes of herbicides, like picolinic acid salts (e.g. Tordon K produced by Dow Chemical Company) which are used in summer foliage treatment, are not normally oil-soluble. In order to apply these herbicides, additional carriers other than fuel oils must be kept available.

An object of the present invention is to provide a dilutant which is an effective carrier of relatively high quantities of herbicides, thus minimizing costly use of large volumes of carrier solutions and their resulting potentially damaging side effects, while also minimizing use of costly spray equipment, and personnel required to transport and use large quantities of fuel oil.

A further object of the present invention is to provide a dilutant which is capable of carrying a variety of herbicides, therby eliminating the need of maintaining and transporting stocks of a number of different dilutants for different herbicides.

An additional object of the present invention is to provide a dilutant which is both hydrophilic and lipophilic and capable of penetrating bark and woody plant tissue while retaining the herbicide and allowing the active ingredients to move upward within the xylem and downward through the phloem of the plant. This significantly reduces the labor and costs involved in preparing an area for treatment.

Another object of the present invention is to provide a dilutant which may function as a carrier for herbicides, insecticides, fungicides, and plant growth regulators.

SUMMARY OF THE INVENTION

In the present invention there is provided a dilutant composed of lecithin, a hydrocarbon filler, and a mixture of emulsifiers, pine oils or terpenes, and heavy aliphatic mineral oils. The resulting solution readily mixes with oil-soluble or emulsifiable industrial herbicides. Substitution of the present invention as a herbicide carrier in place of fuel oils currently employed requires 1/10 to 1/25 the quantity of dilutant to effectively disperse the same operative amount of herbicide. The affinity of the dilutant for herbicides also assures that separation will not occur during storage and handling, even at prolonged low temperatures.

The unique combination of chemicals utilized in the present invention creates a dilutant which is both hydrophilic and lipophilic. These properties allow the dilutant to penetrate bark and woody plant tissue while retaining the herbicide, and permit the active ingredients to move upward through the xylem and downward through the phloem of the plant. Thus, basal application of herbicide mixed in a dilutant made in accordance with the present invention does not require time-consuming cutting or frilling preparation of the target plants.

The present invention not only functions as an effective dilutant for a number of varieties of herbicides, but also may be used as a dilutant for fungicides, insecticides, and plant growth regulators.

The present invention provides considerable cost savings by greatly reducing the quantity of dilutant required, reducing the variety of dilutants which must be stocked, reducing the amount of preparation work prior to application, and reducing the maintenance, transportation, and handling costs of herbicide-dilutant mixtures. Additionally, many side-effects, such as odor and damage from off-target drift, are minimized or eliminated.

DETAILED DESCRIPTION OF THE INVENTION

A dilutant for herbicides is provided. The dilutant (or "carrier") is produced by mixing certain chemical components into a solution. The solution has a high affinity for both emulsifiable and oil-soluble industrial herbicides and may be used in either basal bark or cut surface treatment of nonagricultural areas.

The dilutant includes three categories of ingredients: hydrocarbon filler, lecithin, and a mixture of other chemicals.

Approximately 50% by weight of the dilutant (within a broad possible range of 20–80%, but preferably 30% to 70%) consists of a hydrocarbon filler, such as white kerosene. This is provided to dilute the other ingredients and lower the viscosity of the dilutant. The filler may be either an aliphatic hydrocarbon (e.g. kerosene, or diesel oil) or an aromatic hydrocarbon (e.g. xylene, or Tenneco 500, made by Tenneco Chemicals, Inc.) and may include alcohols or fuel oils.

Approximately 25% by weight of the dilutant (within a broad possible range of 10–40%, but preferably 15% to 30%) consists of lecithin, such as Alcolec S, produced by American Lecithin Company, Atlanta, Ga.

Approximately 25% by weight of the dilutant (within a broad possible range of 10–40%, but preferably 15% to 30%) consists of a mixture of other chemicals. This mixture contains: about 20% emulsifiers (within a range of 12% to 32%), such as T-Mulz 808-A, produced by Thompson-Hayward Company; about 12% pine oils (within a range of 8–20%), such as Pynol, produced by Reichhold Chemicals, Inc., or terpenes, such as Terpinol; and about 68% heavy aliphatic mineral oils (within a range of 45–80%), such as Orchex Spray Oil, produced by Exxon Corporation, and Sunspray 11N, produced by Sun Oil Company.

The dilutant is produced by combining the above ingredients at ambient temperature and pressure and mixing until a homogenous solution results. The chemical components need not be added in any particular order.

The present invention has a high affinity for emulsifiable and oil-soluble industrial herbicides. It has been found to be compatible with: Garlon 4, Tordon K, and Tordon 101, all produced by Dow Chemical Company; Weedone 2,4-DP, and Weedone LV-4, both produced by Union Carbide Agricultural Products Company; Banvel 520, produced by Velsicol Chemical Corporation; Super Brush Killer, produced by PBI/Gordon Corporation; and Eptam 7E, produced by Stauffer Chemical Company. Members of the picolinic acid salts group, such as Tordon K and Tordon 101, which are typically used in foliage treatment, are not normally soluble in oil.

In most cases, the herbicide can be effectively mixed with the dilutant up to a 1:1 ratio. However, 20–25% herbicide in the solution is the preferred application. This produces a vast improvement over the 1:50 to 1:100 ratio previously required in certain applications with fuel oil dilutants. The present invention's affinity for herbicide is so great that separation will not normally occur during storage or handling, even at prolonged low temperature. Mixing is accomplished through the standard procedure of combining the desired proportions and shaking, stirring, or mechanically agitating.

The present invention creates a dilutant which is both hydrophilic and lipophilic. These properties provide the dilutant with a unique ability to penetrate bark and woody plant tissue while carrying the herbicide along with it and thereby allowing movement upward in the xylem as well as downward in the phloem. In most basal applications, where the herbicide is applied around the treated plant, the unique quality of the dilutant to penetrate the bark avoids the need to frill or cut in preparation for spraying. Basal bark applications using this technique have proven very effective—with a kill rate in excess of 90%.

Although the present invention was designed primarily as a carrier for non-agricultural herbicides, it functions equally well as a dilutant for emulsifiable or oil-soluble insecticides, fungicides, and plant growth regulators. The present invention has been found to be compatible with: insecticides such as Imidan, produced by Stauffer Chemical Company, and Dursban, produced by Dow Chemical Company; fungicides such as Terrazole, produced by Uniroyal, Inc.; and plant growth regulators such as Embark 2S, produced by Minnesota Mining and Manufacturing Company, and Clipper, produced by ICI America, Inc.

By way of example, the following mixtures have been employed and have proven effective.

EXAMPLE 1

A mixture of 20% herbicides Garlon 4 and 80% Basal Oil comprising:

| Constituent | Composition (% by volume) |
| --- | --- |
| Garlon 4 | 20.0% |
| Lecithin (Diglycerides of stearic, palmitic and oleic acid, linked to the choline ester of phosphoric acid) | 20.0 |
| Pine Oil (Terpene alcohols and terpene hydrocarbons) | 2.0 |
| Polyoxyethylene sorbitan fatty acid ester | 3.4 |
| Paraffinic petroleum oil ("crop oil") | 14.6 |
| Kerosene | 40.0 |
|  | 100.0% |

Garlon 4 is a Dow Chemical Company herbicide composed of 61.6% butoxyethyl ester of triclopyr and 38.4% inert ingredients.

This mixture is employed using standard spray equipment and applying the chemicals around the circumference of the base of the targeted trees as a mist. Run off should be avoided. Application is at a rate of three (3) gallons per acre. Use of the mixture in this manner has produced the folowing test results:

| Plant | Kill Rate (%) |
| --- | --- |
| Sumac | 100% |
| Elm | 100 |
| Maple | 98 |
| Sassafras | 96 |
| Boxelder | 92 |
| Ash | 86 |
| Birch | 83 |
| Cherry | 83 |
| Hickory | 80 |
| Oak | 79 |

EXAMPLE 2

A mixture of 20% Garlon 4, 20% Weedone 170, and 60% Basal Oil comprising

| Constituent | Composition (% by volume) |
| --- | --- |
| Garlon 4 | 20.00 |
| Weedone 170 | 20.00 |
| Lecithin | 15.00 |
| Pine Oil | 1.50 |
| Polyoxyethylene sorbitan fatty acid ester | 2.55 |
| Paraffinic petroleum oil | 10.95 |
| Kerosene | 30.00 |
|  | 100.00% |

Weedone 170 is a Union Carbide agricultural chemical composed of 59.2% active herbicides and 40.8% inert ingredients.

Use of this mixture in the low volume method set forth above has produced the following test results:

| Plant | Kill Rate (%) |
| --- | --- |
| Oak | 100% |
| Elm | 100 |
| Maple | 98 |

-continued

| Plant | Kill Rate (%) |
| --- | --- |
| Sumac | 98 |
| Sassafras | 97 |
| Alder | 96 |
| Ash | 96 |
| Cherry | 95 |
| Boxelder | 92 |
| Hickory | 68 |

Examples of combinations with other pesticides which are believed to provide effective low volume treatment include:

EXAMPLE 1

A mixture of 10% Cythion 57% EC and 90% Basal Oil comprising

| Constituent | Composition (% by volume) |
| --- | --- |
| Cythion 57% EC | 10.0% |
| Lecithin | 22.5 |
| Pine Oil | 2.2 |
| Polyoxyethylene sorbitan fatty acid ester | 3.8 |
| Paraffinic petroleum oil | 16.4 |
| Kerosene | 45.1 |
|  | 100.0% |

Cythion 57% EC is an insecticide produced by American Cyanamid Company used to control caterpillars, bagworms, and leaf miner insects. It contains 57% malathion, 30% xylene and 13% emulsifiers.

EXAMPLE 2

A mixture of 5% Clipper 20UL and 95% Basal Oil comprising

| Constituent | Composition (% by volume) |
| --- | --- |
| Clipper 20UL | 5.0% |
| Lecithin | 23.8 |
| Pine Oil | 2.4 |
| Polyethoxylated tall oil fatty acid ester | 4.0 |
| Paraffinic petroleum oil | 17.3 |
| Kerosene | 47.5 |
|  | 100.0% |

Clipper 20UL is a tree growth retardant for ornamental trees produced by ICI Americas, Inc. It contains 2.51% paclobutrazol and 97.49% methanol.

While a particular embodiment of the present invention has been disclosed herein, it is not intended to limit the invention to such a disclosure, and changes and modifications may be incorporated and embodied within the scope of the following claims.

What I claim is:

1. A non-agricultural dilutant and carrier for low volume basal bark application of herbicides, fungicides, insecticides and plant growth regulators to woody plants comprising
   20% to 80% by weight of a hydrocarbon filler,
   10% to 40% by weight of lecithin, and
   10% to 40% by weight of a mixture of emulsifiers, pine oils or terpenes, and mineral oils.

2. Composition in accordance with claim 1 wherein said hydrocarbon filler includes aromatic or aliphatic hydrocarbons, the addition of which lowers the viscosity of said dilutant.

3. Composition in accordance with claim 1 wherein said mixture includes
   12% to 32% by weight of emulsifiers,
   8% to 20% by weight of pine oils or terpenes, and
   45% to 80% by weight of mineral oils.

4. Composition in accordance with claim 1 wherein said dilutant comprises
   30% to 70% by weight of a hydrocarbon filler,
   15% to 30% by weight of lecithin, and
   15% to 30% by weight of a mixture of emulsifiers, pine oils or terpenes, and mineral oils.

5. A method of basal application of a pesticide, selected from the group of herbicides, insecticides, fungicides and plant growth regulators, to woody plants, comprising
   providing a mixture of said pesticide and a non-agricultural dilutant, said dilutant comprising
   20% to 80% by weight of a hydrocarbon filler,
   10% to 40% by weight of lecithin, and
   10% to 40% by weight of a mixture of emulsifiers, pine oils or terpenes, and mineral oils,
   said mixture of pesticide to dilutant comprising 5 to 40% by volume of a commercial pesticide to said dilutant; and
   applying said mixture to the plants at a low volume to avoid run down of the mixture.

6. A method in accordance with claim 5 wherein said hydrocarbon filler includes aromatic or aliphatic hydrocarbons, the addition of which lowers the viscosity of said dilutant.

7. A method in accordance with claim 5 wherein said mixture includes
   12% to 32% by weight of emulsifiers,
   8% to 20% by weight of pine oils or terpenes, and
   45% to 80% by weight of mineral oils.

8. A method in accordance with claim 5 wherein said dilutant comprises
   30% to 70% by weight of a hydrocarbon filler,
   15% to 30% by weight of lecithin, and
   15% to 30% by weight of a mixture of emulsifiers, pine oils or terpenes, and mineral oils.

9. A method in accordance with claim 5 wherein said low volume application comprises misting the plants using conventional spray equipment.

* * * * *